US012793828B2

(12) United States Patent
Kruse et al.

(10) Patent No.: US 12,793,828 B2
(45) Date of Patent: Nov. 10, 2026

(54) SYSTEMS AND METHODS OF PAIRING DEVICES IN AN AMBULATORY INFUSION PUMP SYSTEM

(71) Applicant: Tandem Diabetes Care, Inc., San Diego, CA (US)

(72) Inventors: Geoffrey A. Kruse, San Diego, CA (US); Thomas R. Ulrich, Oceanside, CA (US); Jason Farnan, San Diego, CA (US); Robert Eastridge, San Diego, CA (US); Michael Michaud, San Diego, CA (US); Dwight Lee, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 522 days.

(21) Appl. No.: 16/879,927

(22) Filed: May 21, 2020

(65) Prior Publication Data

US 2020/0372995 A1 Nov. 26, 2020

Related U.S. Application Data

(60) Provisional application No. 62/850,811, filed on May 21, 2019.

(51) Int. Cl.

| | |
|---|---|
| ***G16H 20/17*** | (2018.01) |
| ***A61M 5/172*** | (2006.01) |
| ***G06F 21/60*** | (2013.01) |
| ***G06F 21/62*** | (2013.01) |

(52) U.S. Cl.
CPC .......... *G16H 20/17* (2018.01); *A61M 5/1723* (2013.01); *G06F 21/606* (2013.01); *G06F 21/62* (2013.01); *A61M 2005/1726* (2013.01); *A61M 2205/3553* (2013.01); *A61M 2205/6009* (2013.01)

(58) Field of Classification Search
CPC ................ G16H 20/17; A61M 5/1723; A61M 2005/1726; A61M 2205/3553; A61M 2205/6009; G06F 21/606; G06F 21/62
See application file for complete search history.

(56) References Cited

U.S. PATENT DOCUMENTS

| | | | |
|---|---|---|---|
| 5,191,719 | A | 3/1993 | Kitt |
| 6,012,034 | A | 1/2000 | Hamparian et al. |
| 7,364,566 | B2 | 4/2008 | Elkins et al. |
| 7,826,382 | B2 | 11/2010 | Sicurello et al. |
| 7,928,850 | B2 | 4/2011 | Hayter et al. |
| 8,016,740 | B2 | 9/2011 | Connors et al. |
| 8,095,197 | B2 | 1/2012 | Santini, Jr. et al. |
| 8,121,857 | B2 | 2/2012 | Galasso et al. |
| 8,149,117 | B2 | 4/2012 | Fennell et al. |

(Continued)

*Primary Examiner* — Robert A Sorey
*Assistant Examiner* — Kristine K Rapillo
(74) *Attorney, Agent, or Firm* — Straylight LLP

(57) ABSTRACT

Disclosed herein are methods for establishing communication protocols between wireless devices in infusion pump systems. Infusion pump systems can include a number of components capable of wireless communication with one or more other components including an infusion pump, a continuous glucose monitoring (CGM) system, a smartphone or other remote consumer electronic device and/or a dedicated remote controller for the infusion pump. The present disclosure provides various methods for simplifying connections among these devices.

21 Claims, 10 Drawing Sheets

(56) References Cited

U.S. PATENT DOCUMENTS

| | | | | |
|---|---|---|---|---|
| 8,287,495 | B2 | 10/2012 | Michaud et al. | |
| 8,372,351 | B2 | 2/2013 | Ow-Wing | |
| 8,401,194 | B2 | 3/2013 | Nierzwick et al. | |
| 8,414,563 | B2 | 4/2013 | Kamen et al. | |
| 8,444,595 | B2 | 5/2013 | Brukalo et al. | |
| 8,449,523 | B2 | 5/2013 | Brukalo et al. | |
| 8,454,554 | B2 | 6/2013 | Reinke | |
| 8,456,301 | B2 | 6/2013 | Fennell | |
| 8,461,985 | B2 | 6/2013 | Fennell et al. | |
| 8,573,027 | B2 | 11/2013 | Rosinko et al. | |
| 8,932,250 | B2 | 1/2015 | Montgomery | |
| 8,986,253 | B2 | 3/2015 | DiPerna | |
| 9,049,982 | B2 | 6/2015 | Brukalo | |
| 9,173,992 | B2 | 11/2015 | Bengtsson | |
| 9,381,297 | B2 | 7/2016 | Brown et al. | |
| 9,474,856 | B2 | 10/2016 | Blomquist | |
| 9,486,571 | B2 | 11/2016 | Rosinko | |
| 9,565,718 | B2 | 2/2017 | Swanson | |
| 9,737,656 | B2 | 8/2017 | Rosinko | |
| 9,980,140 | B1 * | 5/2018 | Spencer | H04W 12/02 |
| 10,213,547 | B2 | 2/2019 | Rosinko | |
| 10,279,106 | B1 | 5/2019 | Cook et al. | |
| 10,430,043 | B2 | 10/2019 | Rosinko et al. | |
| 10,478,551 | B2 | 11/2019 | Rosinko | |
| 10,524,110 | B1 * | 12/2019 | Klem | H04W 12/062 |
| 10,736,037 | B2 | 8/2020 | Kruse et al. | |
| 10,773,015 | B2 | 9/2020 | Blomquist et al. | |
| 10,806,851 | B2 | 10/2020 | Rosinko | |
| 10,888,655 | B2 | 1/2021 | Farnan et al. | |
| 10,918,785 | B2 | 2/2021 | Rosinko | |
| 11,039,491 | B2 * | 6/2021 | Zheng | A61M 5/14248 |
| 2008/0312584 | A1 | 12/2008 | Montgomery | |
| 2009/0240193 | A1 | 9/2009 | Mensinger et al. | |
| 2010/0069730 | A1 | 3/2010 | Bergstrom | |
| 2010/0198142 | A1 | 8/2010 | Sloan et al. | |
| 2010/0198183 | A1 | 8/2010 | Lanigan et al. | |
| 2010/0234708 | A1 | 9/2010 | Buck | |
| 2010/0274323 | A1 | 10/2010 | Williamson | |
| 2010/0292556 | A1 | 11/2010 | Golden | |
| 2010/0305421 | A1 | 12/2010 | Ow-Wing | |
| 2010/0331646 | A1 | 12/2010 | Hoss | |
| 2010/0331651 | A1 | 12/2010 | Groll | |
| 2010/0331652 | A1 | 12/2010 | Groll et al. | |
| 2011/0044333 | A1 | 2/2011 | Sicurello et al. | |
| 2011/0071372 | A1 | 3/2011 | Sloan et al. | |
| 2011/0190694 | A1 | 8/2011 | Lanier, Jr. et al. | |
| 2012/0095393 | A1 | 4/2012 | Reinke | |
| 2012/0232520 | A1 | 9/2012 | Sloan et al. | |
| 2013/0053816 | A1 | 2/2013 | Diperna et al. | |
| 2013/0324928 | A1 | 12/2013 | Kruse | |
| 2014/0054883 | A1 | 2/2014 | Lanigan et al. | |
| 2014/0113553 | A1 | 4/2014 | Brukalo | |
| 2015/0174320 | A1 | 6/2015 | Grant | |
| 2016/0004390 | A1 | 1/2016 | Laska | |
| 2016/0271325 | A1 | 9/2016 | Farnan et al. | |
| 2016/0339172 | A1 | 11/2016 | Michaud et al. | |
| 2017/0049957 | A1 | 2/2017 | Michaud | |
| 2017/0127462 | A1 | 5/2017 | Liu | |
| 2018/0137252 | A1 * | 5/2018 | Mairs | G16H 40/63 |
| 2018/0137938 | A1 | 5/2018 | Vaddiraju | |
| 2019/0054236 | A1 * | 2/2019 | Estes | G16Z 99/00 |
| 2019/0183434 | A1 * | 6/2019 | Sjolund | A61B 5/14532 |
| 2019/0321545 | A1 | 10/2019 | Saint | |
| 2019/0321552 | A1 | 10/2019 | DiPerna et al. | |
| 2020/0009319 | A1 | 1/2020 | Ludolph | |
| 2020/0009320 | A1 | 1/2020 | Ludolph | |
| 2020/0101224 | A1 | 4/2020 | Lintereur | |
| 2020/0162896 | A1 * | 5/2020 | Su | A61B 5/0022 |
| 2020/0206420 | A1 | 7/2020 | Michaud | |
| 2020/0306445 | A1 | 10/2020 | Michaud et al. | |
| 2020/0329433 | A1 | 10/2020 | Kruse et al. | |

* cited by examiner

SYSTEMS AND METHODS OF PAIRING DEVICES IN AN AMBULATORY INFUSION PUMP SYSTEM

RELATED APPLICATION

The present application claims the benefit of U.S. Provisional Application No. 62/850,811 filed May 21, 2019, which is hereby incorporated herein in its entirety by reference.

TECHNICAL FIELD

The present invention relates to medical pumps for delivering medicament to a patient, and more specifically, to systems in which a user-wearable pump wirelessly communicates with other devices.

BACKGROUND

There are a wide variety of medical treatments that include the administration of a therapeutic fluid in precise, known amounts at predetermined intervals. Devices and methods exist that are directed to the delivery of such fluids, which may be liquids or gases, are known in the art.

One category of such fluid delivery devices includes insulin injecting pumps developed for administering insulin to patients afflicted with type I, or in some cases, type II diabetes. Some insulin injecting pumps are configured as portable or ambulatory infusion devices can provide continuous subcutaneous insulin injection and/or infusion therapy as an alternative to multiple daily injections of insulin via a syringe or an insulin pen. Such pumps are worn by the user and may use replaceable cartridges. In some embodiments, these pumps may also deliver medicaments other than, or in addition to, insulin, such as glucagon, pramlintide, and the like. Examples of such pumps and various features associated therewith include those disclosed in U.S. Patent Publication Nos. 2013/0324928 and 2013/0053816 and U.S. Pat. Nos. 8,287,495; 8,573,027; 8,986,253; and 9,381,297, each of which is incorporated herein by reference in its entirety.

Another type of pump that has been developed is a patch pump also known as a micro pump. Patch pumps are small pumps, typically ambulatory, that may be carried directly on the skin under the user's clothing. In some cases, the pumps are situated directly on, or very near to, the injection site such that little or no tubing is required to deliver the insulin or other medicament to the patient. Some patch pumps include a single button on the pump to initiate delivery of medicament and do not include a built-in display or user interface. These pumps are therefore primarily remote-controlled.

With the proliferation of handheld electronic devices, such as mobile phones (e.g., smartphones), there is a desire to be able to remotely utilize such devices to optimize usage of infusion pumps, including both patch pumps and pumps having their own user interfaces. These remote controllers would enable a pump to be monitored, programmed and/or operated more privately, more conveniently and more comfortably. Accordingly, one potential use of dedicated remote devices and handheld consumer electronic devices (such as smartphones, tablets and the like) is to utilize such devices as controllers for remotely programming and/or operating infusion pumps. In addition to mobile control devices such as smartphones and dedicated remote controllers, it may be beneficial to enable infusion pumps to communicate with other devices, such as continuous glucose monitors, glucose meters, and other health monitoring devices, for example.

To use a smartphone or dedicated remote control device to control an infusion pump, the device must be paired with the particular pump in order to enable the pump to execute commands sent by the remote device. Other devices, such as continuous glucose monitors must also be paired in order to be used in conjunction with the pump. Due to security requirements, a simple Bluetooth pairing is typically not sufficient to pair devices with a pump and an additional step, such as entering a complex code displayed on the pump into the phone or other device must be undertaken to securely pair the devices. In a system that includes multiple devices such as a phone, dedicated remote control and a CGM, such a process can therefore be time consuming.

SUMMARY

Disclosed herein are methods for establishing communication protocols between wireless devices in infusion pump systems. Infusion pump systems can include a number of components capable of wireless communication with one or more other components including an infusion pump, a continuous glucose monitoring (CGM) system, a smartphone or other remote consumer electronic device and/or a dedicated remote controller for the infusion pump. The present disclosure provides various methods for simplifying connections among these devices.

In embodiments, a system and method simplify the connection of additional devices into an infusion pump system having multiple devices. After a pump is securely paired with a primary device such as, for example, a smartphone, the primary device can be enabled to share the secure connection information with one or more secondary devices. The one or more secondary devices can then automatically be paired with the pump when connecting to the pump because the required secure connection information is already present on the secondary device and therefore does not need to be manually entered or otherwise acquired as was done with the primary device. By enabling the security feature such as a complex security code to be shared with secondary devices from the primary device rather than reenacting the initial pairing procedure on the secondary devices, significant time and effort can be saved while still ensuring secure connections.

In an embodiment, a method of pairing devices in an ambulatory infusion pump system, can include initiating a pairing procedure to pair a user-wearable infusion pump with a primary device, receiving secure connection information for pairing the user-wearable infusion pump with the primary device at the primary device and verifying the secure connection information to pair the user-wearable pump with the primary device. If a pairing procedure to pair the user-wearable infusion pump with a secondary device is initiated, the primary device can share the secure connection information with the secondary device. The secondary device can then be paired with the user-wearable infusion pump using the secure connection information received from the primary device.

In an embodiment, a method of pairing devices in an ambulatory infusion pump system can include initiating a pairing procedure to pair a user-wearable infusion pump with a primary device and executing the pairing procedure including executing a security protocol on the primary device. If a pairing procedure to pair the user-wearable infusion pump with a secondary device is initiated, the primary device can share secure connection information with the secondary device. The secondary device can then be paired with the user-wearable infusion pump using the secure connection information received from the primary device without executing the security protocol on the secondary device.

In embodiments, systems that may include more than one individual having a device capable of communicating with and/or controlling an infusion pump can be configured to provide different individuals with different levels of access and/or control of pump functions and/or data. A primary device can be securely paired with an infusion pump and provided with a master key giving full pump access to the primary device, including the ability to provide other devices with varying levels of access to the pump. If a secondary device of another user is to be given a different level of access to the pump, the user of the primary device can select a level of access for the secondary device and share a different, secondary security key with the secondary device rather than the master key. The pump can then be capable of being controlled and/or accessed by multiple devices having different levels of access based on the specific security key that was provided by the primary device and used to pair the secondary device with the pump.

In embodiments, the pairing process between an infusion pump and a device including a camera, such as a smartphone, can be simplified. When a security code is displayed on the pump such as a complex, e.g., 16 digit, security key as a part of the pairing process, rather than the user manually entering the security key into the phone, the user can employ the camera of the phone to scan the security key while it is displayed on the screen of the pump. This can be done, for example, by using the camera to take a picture of the code and the phone automatically recognizing the characters in the code. The scanned security data is then used by the phone to complete the pairing process. This enables a user to quickly pair the phone with the pump while also eliminating the possibility of typographical errors in transposing the security key into the phone.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
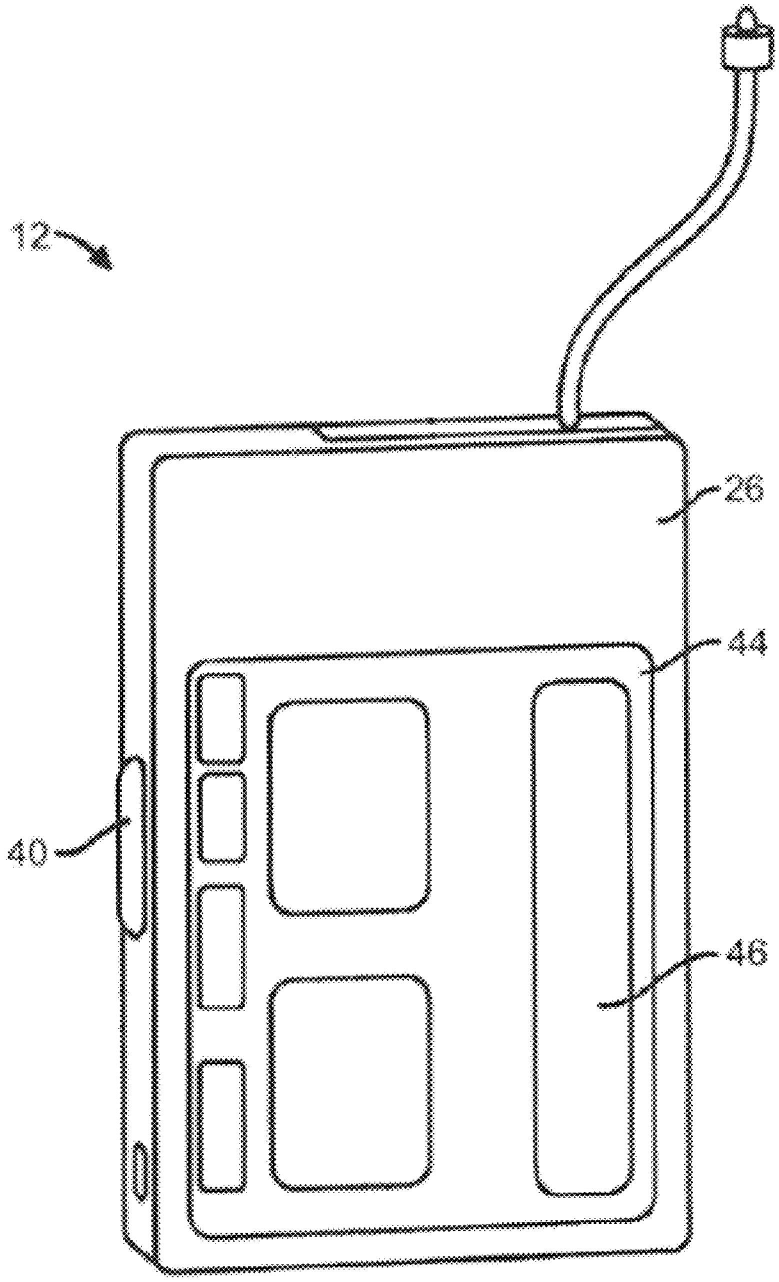
FIG. 1 depicts an embodiment of a pump system according to the disclosure.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The following detailed description should be read with reference to the drawings in which similar elements in different drawings are numbered the same. The drawings, which are not necessarily to scale, depict illustrative embodiments and are not intended to limit the scope of the invention.

FIG. 1 depicts an embodiment of a medical device according to the disclosure. In this embodiment, the medical device is configured as a pump 12. Pump 12 may be an infusion pump that includes a pumping or delivery mechanism and reservoir for delivering medicament to a patient and an output/display 44. The output/display 44 may include an interactive and/or touch sensitive screen 46 having an input device such as, for example, a touch screen comprising a capacitive screen or a resistive screen. The pump 12 may additionally or instead include one or more of a keyboard, a microphone or other input devices known in the art for data entry, some or all of which may be separate from the display. The pump 12 may also include a capability to operatively couple to one or more other display devices such as a remote display, a remote control device, a laptop computer, personal computer, tablet computer, a mobile communication device such as a smartphone, a wearable electronic watch or electronic health or fitness monitor, or personal digital assistant (PDA), a CGM display etc.

In one embodiment, the medical device can be an ambulatory insulin pump configured to deliver insulin to a patient. Further details regarding such pump devices can be found in U.S. Pat. No. 8,287,495, which is incorporated herein by reference in its entirety. In other embodiments, the medical device can be an infusion pump configured to deliver one or more additional or other medicaments to a patient.

Figure 2:
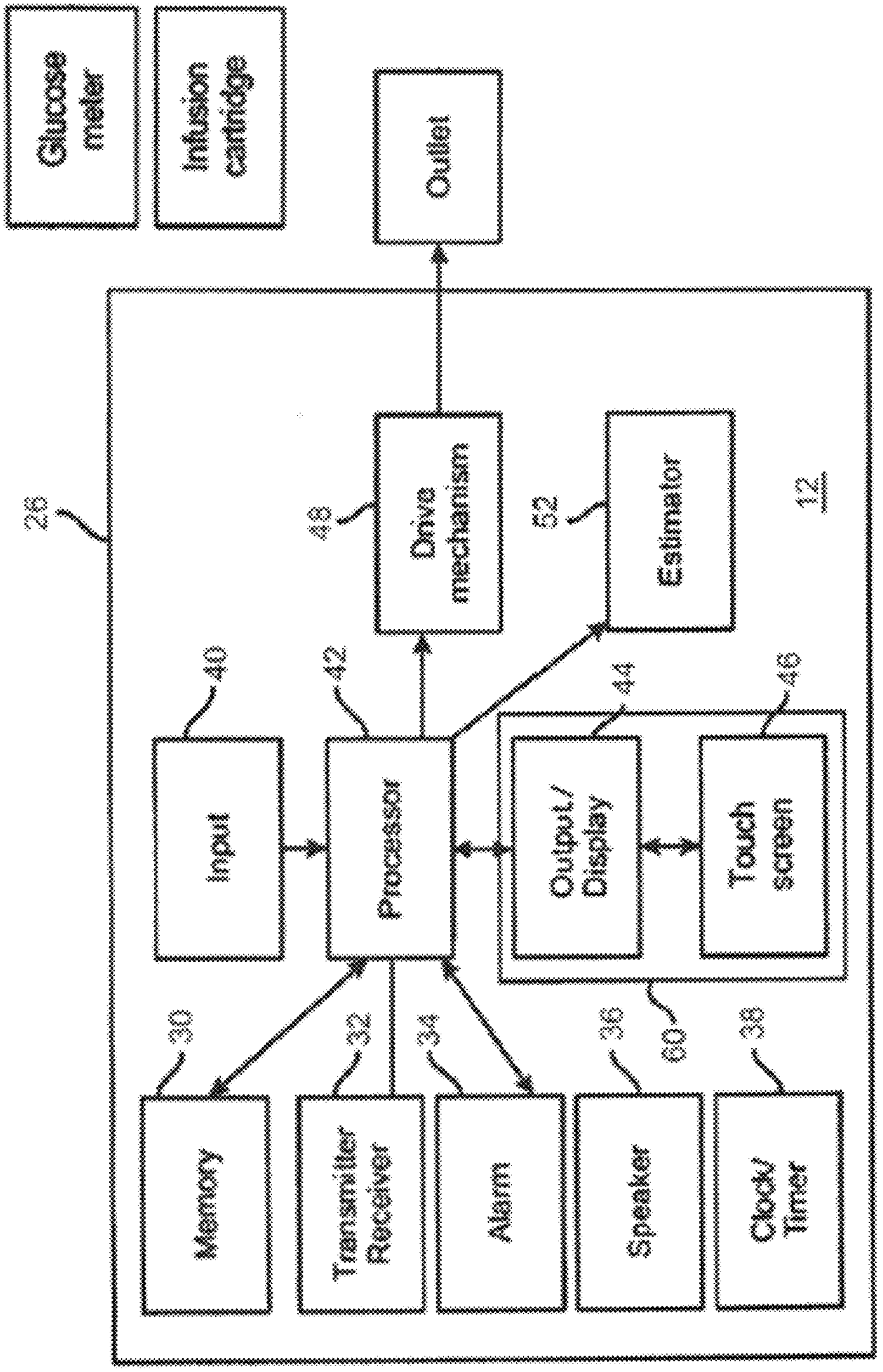
FIG. 2 depicts a block diagram representing an embodiment of a pump system according to the disclosure.

FIG. 2 illustrates a block diagram of some of the features that can be used with embodiments, including features that may be incorporated within the housing 26 of a medical device such as a pump 12. The pump 12 can include a processor 42 that controls the overall functions of the device. The infusion pump 12 may also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface is a graphical user interface (GUI) 60 having a touch sensitive screen 46 with input capability. In some embodiments, the processor 42 may communicate with one or more other processors within the pump 12 and/or one or more processors of other devices, for example, a continuous glucose monitor (CGM), display device, smartphone, etc. through the transmitter/receiver. The processor 42 may also include programming that may allow the processor to receive signals and/or other data from an input device, such as a sensor that may sense pressure, temperature or other parameters.

Figure 3B:
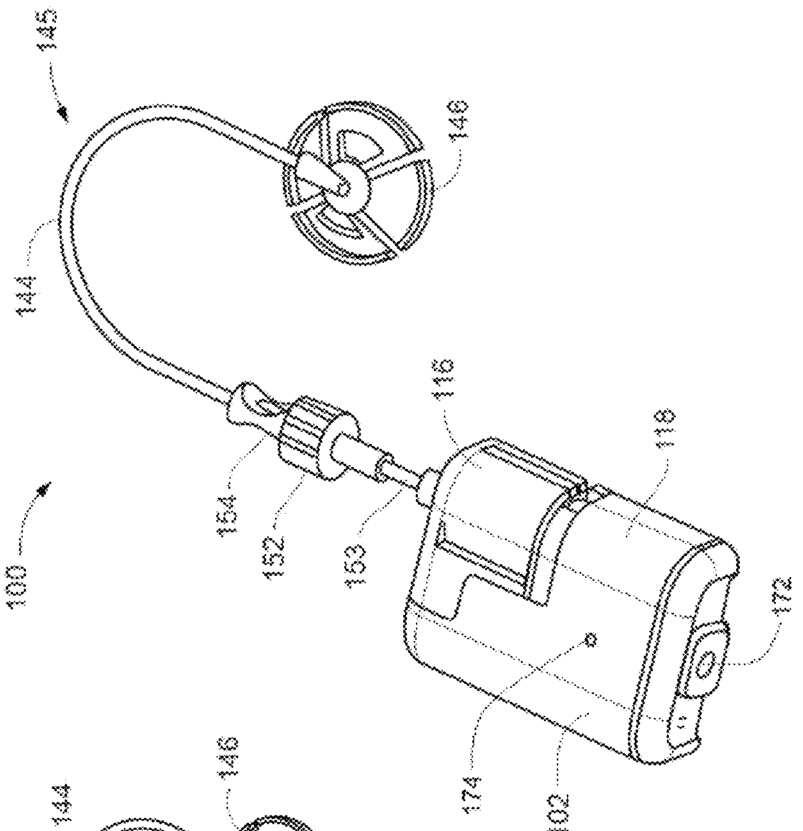
FIGS. 3A-3B depict an embodiment of a pump system according to the disclosure.
Figure 3A:
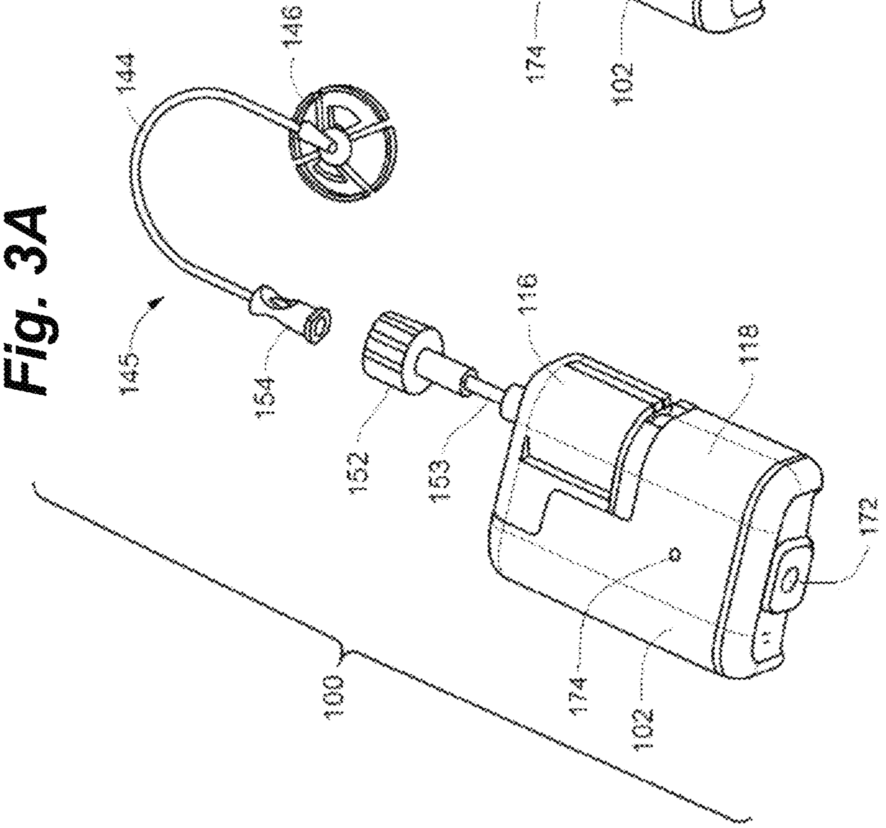

FIGS. 3A-3B depict another pump system including a pump 102 that can be used with embodiments. Drive unit 118 of pump 102 includes a drive mechanism 122 that mates with a recess in disposable cartridge 116 of pump 102 to attach the cartridge 116 to the drive unit 118. Pump system 100 can further include an infusion set 145 having a connector 154 that connects to a connector 152 attached to pump 102 with tubing 153. Tubing 144 extends to a site connector 146 that can attach or be pre-connected to a cannula and/or infusion needle that punctures the patient's skin at the infusion site to deliver medicament from the pump 102 to the patient via infusion set 145. In some embodiments, pump can include a user input button 172 and an indicator light 174 to provide feedback to the user.

In one embodiment, pump 102 includes a processor that controls operations of the pump and, in some embodiments, may receive commands from a separate device for control of operations of the pump. Such a separate device can include, for example, a dedicated remote control or a smartphone or other consumer electronic device executing an application configured to enable the device to transmit operating commands to the processor of pump 102. In some embodiments, processor can also transmit information to one or more separate devices, such as information pertaining to device parameters, alarms, reminders, pump status, etc. In one embodiment pump 102 does not include a display but may include one or more indicator lights 174 and/or one or more input buttons 172. Pump 102 can also incorporate any or all of the features described with respect to pump 12 in FIG. 2. Further details regarding such pumps can be found in U.S. Pat. No. 10,279,106 and U.S. Patent Publication Nos. 2016/0339172 and 2017/0049957, each of which is hereby incorporated herein by reference in its entirety.

Figure 4B:
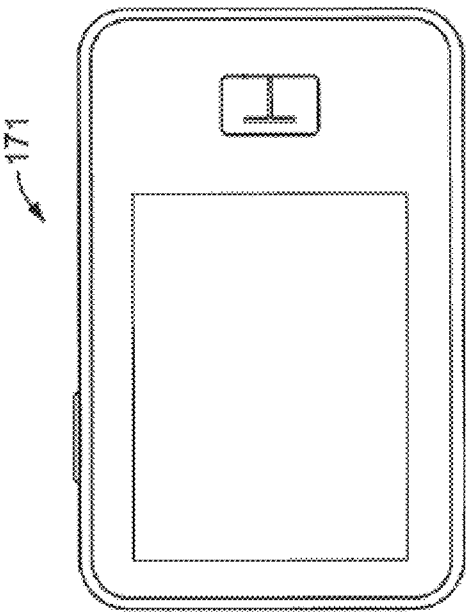
FIGS. 4A-4B depict remote control devices for a pump system according to the disclosure.
Figure 4A:
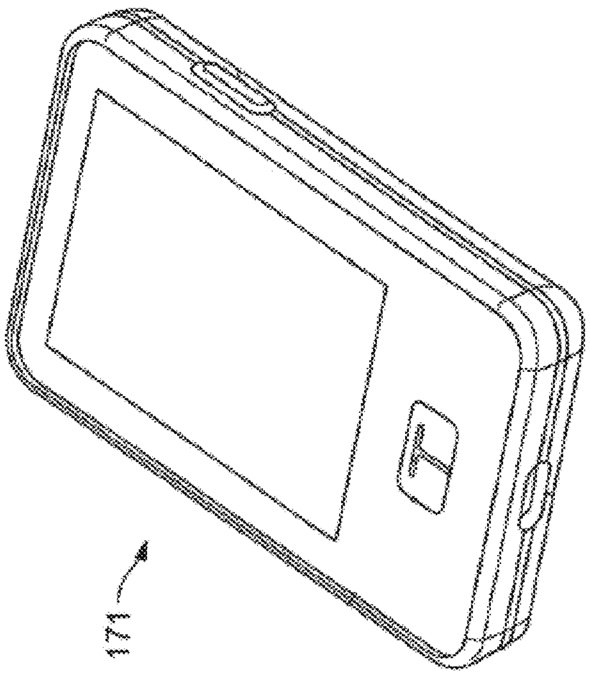
Figure 5:
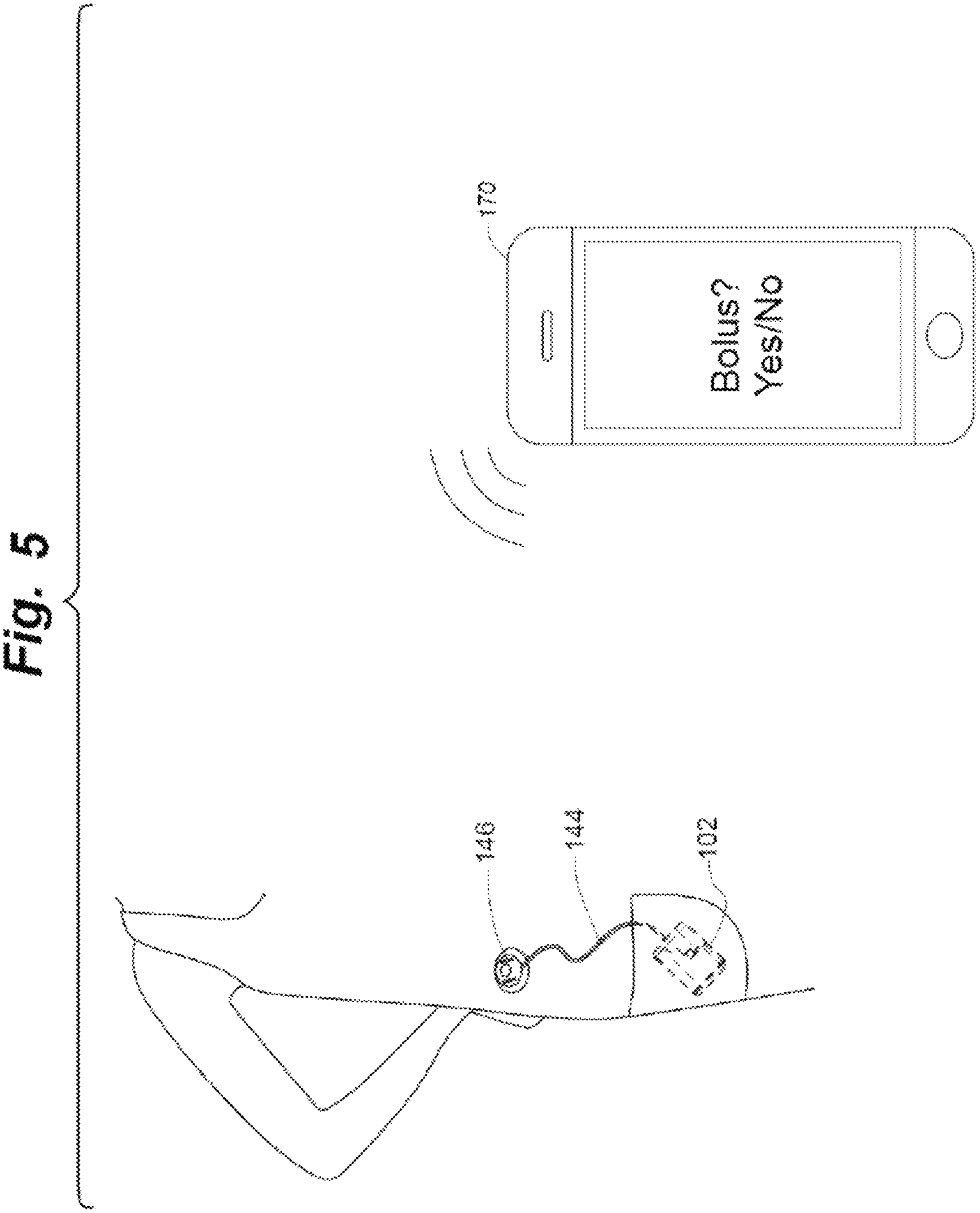
FIG. 5 depicts a schematic representation of a pump system according to the disclosure.

Referring to FIGS. 4A-4B and FIG. 5, one or more remote control devices 170, 171 can be used to communicate with the processor of pump 102 (or pump 12) to control delivery of medicament and transfer data with pump 102 via a wired or a wireless electromagnetic signal, such as via, e.g., a near field communication (NFC) radio frequency (RF) modality or other RF modalities such as Bluetooth®, Bluetooth® low energy, mobile or Wi-Fi communication protocols, for example, according to embodiments of the present disclosure. Such a remote control can include, for example, a mobile communication device 170, such as a smart phone (as depicted in FIG. 5) executing a software application for control of the pump, a dedicated remote controller 171 (as depicted in FIGS. 4A-4B), a wearable electronic watch or electronic health or fitness monitor or personal digital assistant (PDA), etc., or a tablet, laptop or personal computer. Such communications between (and among) the one or more remote control devices 170, 171 and pump 102 may be one-way or two-way for, e.g., effective transfer of data among the devices and the pump, control of pump operations, updating software on the devices and/or pump, and allowing pump-related data to be viewed on the devices and/or pump.

Embodiments of the present disclosure include components capable of and methods using wired and wireless transmission and receipt of signals for exchange of information and commands between and among any of the components as described herein, including, e.g., between a pump and a smartphone; among a pump, a CGM and a smartphone; between a dedicated remote controller and a pump; among a dedicated remote controller, a CGM and a pump; among a dedicated remote controller, a BGM and a pump, and other combinations as would be contemplated by those of skill in the art.

Figure 6:
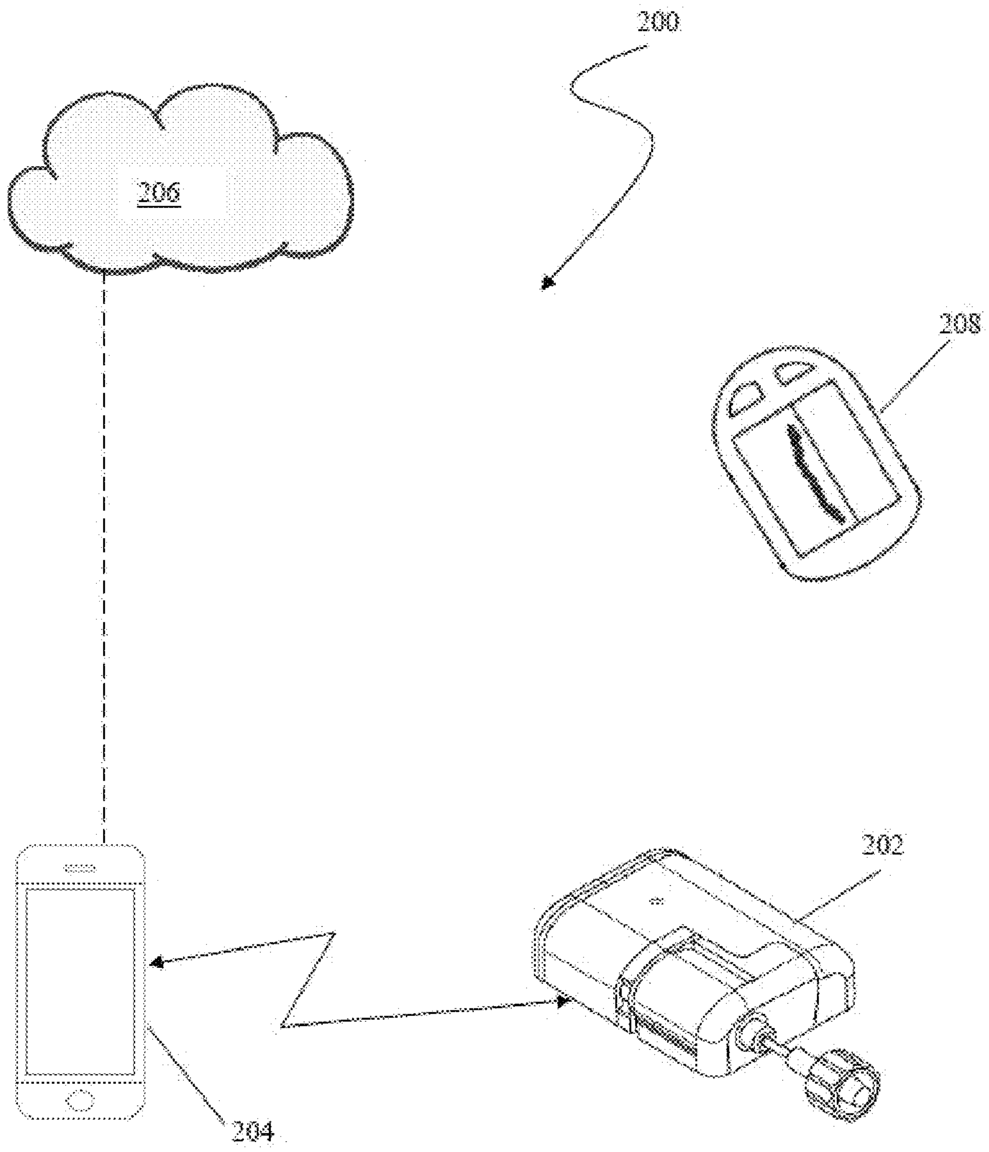
FIG. 6 depicts a schematic representation of a pump system according to the disclosure.

FIG. 6 depicts various components of a pump system 200 according to an embodiment. System components can include, for example, a user-wearable infusion pump 202, a smartphone or other consumer electronic device 204, remote data storage 206 such as the cloud, one or more optional peripheral devices such as a continuous glucose monitor 208, and a dedicated remote controller 210. In the depicted embodiment, the smartphone 204 and/or the dedicated remote controller 210 can obtain data and information from the cloud, such as a medicament delivery control algorithm and communicate control commands and/or information to the infusion pump 202 and receive data and information from the infusion pump 202. As depicted in FIG. 6, the pump 202 can be capable of unidirectional or bidirectional communications via, for example, Bluetooth, with both the remote controller 210 and the smartphone 204. The pump 202 can in various embodiments communicate with a continuous glucose monitor 208 with a corresponding sensor and/or can directly communicate with the CGM sensor. Other optional peripheral devices that can communicate with the pump 202, the smartphone 204 and/or the dedicated remote control device 210 include for example, one or more of a blood glucose meter or other analyte sensing device, an activity or other health monitor, an electronic watch, etc. Although pump 202 is depicted without a display similar to pump 102, pump 202 could also be a pump such as a pump 12 having its own user interface and display.

Figure 7:
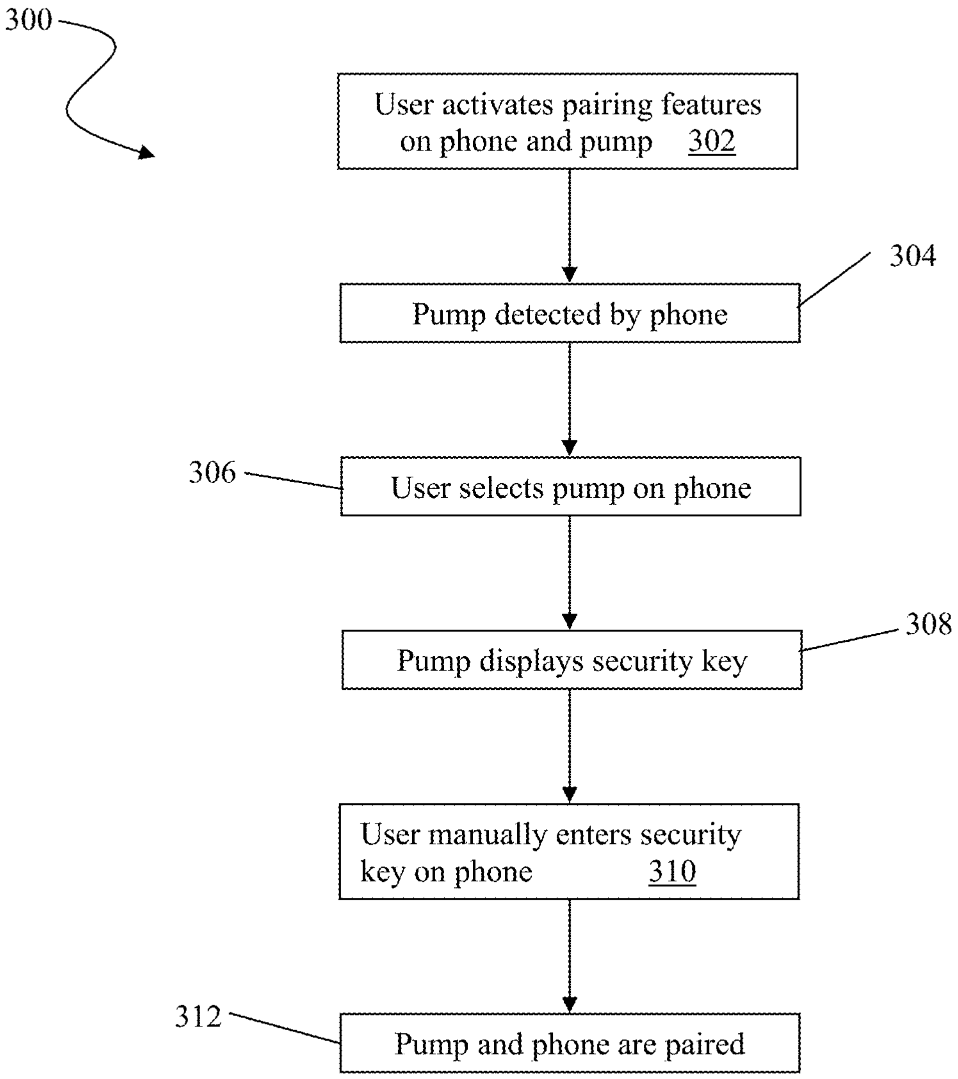
FIG. 7 depicts a flowchart of method steps for pairing an infusion pump with another device according to the disclosure.

For a pump to be able to be controlled by a remote control device such as a smartphone 170 operating a software application for controlling the pump or dedicated remote controller 171 via wireless communication such as, for example, Bluetooth, the pump must be paired with the control device to establish the mutual connection between the devices. Similarly, for the pump and/or remote 170, 171 to communicate with additional devices such as a CGM, the devices must also be paired. One embodiment of such a pairing procedure 300 is depicted in FIG. 7. At step 302, the user activates the pairing features on both the phone and the pump and the phone will then detect the pump at step 304. When the user selects the pump on the phone at step 306 in the phone's pairing feature to initiate device pairing, the pump displays a complex security code on the pump's display at step 308. In one embodiment, the complex security code is a randomized 16-digit string of alphanumeric characters. The user must then manually enter the complex security code into the phone at step 310 and, if the code is entered correctly, the devices are paired at step 312. Although described in the context of pairing a pump and a phone, a similar pairing process could be carried out for pairing any two devices in the system.

Pumps can be paired with remote control devices and other devices through various other secure means and/or through communication of various other types of secure information. One example of a pairing procedure for a pump having no display such that no security code or other information could be viewed on or entered into the pump is described in U.S. patent Publication Ser. No. 16/507,146, which is hereby incorporated herein by reference in its entirety.

Pairing multiples devices with a pump and with each other via a process such as that described with respect to FIG. 7 or other secure connection means can be a time-consuming process. However, the secure pairing is necessary because a simple wireless pairing procedure, such as establishing a Bluetooth connection, does not provide the necessary security and safety for such medical devices. Embodiments of the present disclosure provide for simpler and easier pairing of devices while retaining the required security and safety benefits.

Figure 8:
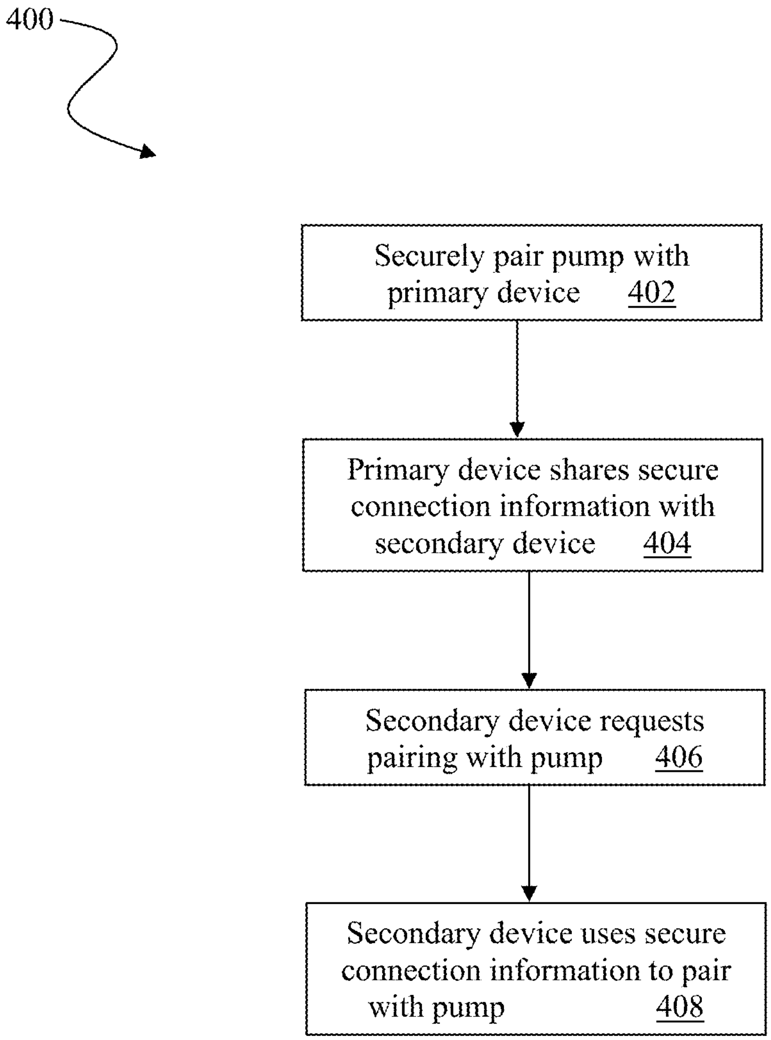
FIG. 8 depicts a flowchart of methods steps for pairing an infusion pump with another device according to the disclosure.

FIG. 8 depicts a flow chart of methods steps for a procedure 400 for pairing multiple devices in an infusion pump system. At step 402, the pump is securely paired with a primary device. In embodiments, this can be done utilizing the pairing procedure 300 of FIG. 7 that employs a complex security code. Alternatively, the devices can be paired using any other secure pairing protocol. The primary device can, for example, be a smartphone having a software application configured to control the pump. It is appreciated that the primary device can be any other device in an infusion pump system. At step 404, the primary device can share the secure connection information, such as the complex security code, with a secondary device. The secure connection information can be shared via, for example, a Bluetooth connection between the primary device and the secondary device.

At step 406, the secondary device can seek to be paired with the pump by wirelessly communicating with the pump. Alternatively, the pump can initiate the connection with the secondary device or the primary device can initiate the connection between the pump and the secondary device. For example, if a phone is the primary device and is already connected to an electronic watch as the secondary device, the phone can initiate pairing between the electronic watch and pump by sharing the secure connection information with the watch. The secondary device can then automatically be paired with the pump at step 408 because the required secure connection information (e.g., complex security code) is already present on the secondary device and/or has already been communicated to the pump and therefore does not need to be manually entered or otherwise obtained by the secondary device as was done with the primary device. A number of secondary devices can be paired in this manner. In an embodiment where the primary device is a smartphone, secondary devices can include, for example, a dedicated remote controller, a continuous glucose monitor, a glucose meter, a fitness tracking device, a tablet or laptop computer and an electronic watch. In various embodiments, any device described herein or known in the art as pairing with an infusion pump can function as the primary device.

The system and method of FIG. 8 simplifies the connection of additional devices into an infusion pump system having multiple devices. By enabling the secure connection feature such as a complex security code to be shared with secondary devices from the primary device rather than the original secure connection being completely reenacted on the secondary devices, significant time and effort can be saved while still ensuring secure connections. Not only is time saved by not requiring repeated manual entry of the code or other secure connection procedure, but in embodiments such as the complex security code of FIG. 7, significant time can be saved because the possibility of typographical errors complicating connections with the secondary devices is removed.

In systems that may employ multiple devices capable of communicating with an infusion pump, there may be more than one individual having a device capable of communicating with and/or controlling the pump. Such individuals can include for example, healthcare providers, caregivers such as parents or grandparents, and patients, including minor patients. Given the varied needs and sophistication levels of different individuals, it may be desirable to provide different individuals with different levels of access and/or control of pump functions and/or data. Such levels can include, for example, read only access to data, bolus only capability for pump programming and full programming access. In addition, an individual user may have more than one device capable of interacting with a pump and it may be desirable to provide different devices with different levels of access and/or functionality. For example, it may be desirable to provide a user's phone with full control of the pump and only enable display only, bolus only, etc. access for another device such as an electronic watch. In an embodiment, wireless pairing procedures as described herein can be utilized to provide such varying access.

Figure 9:
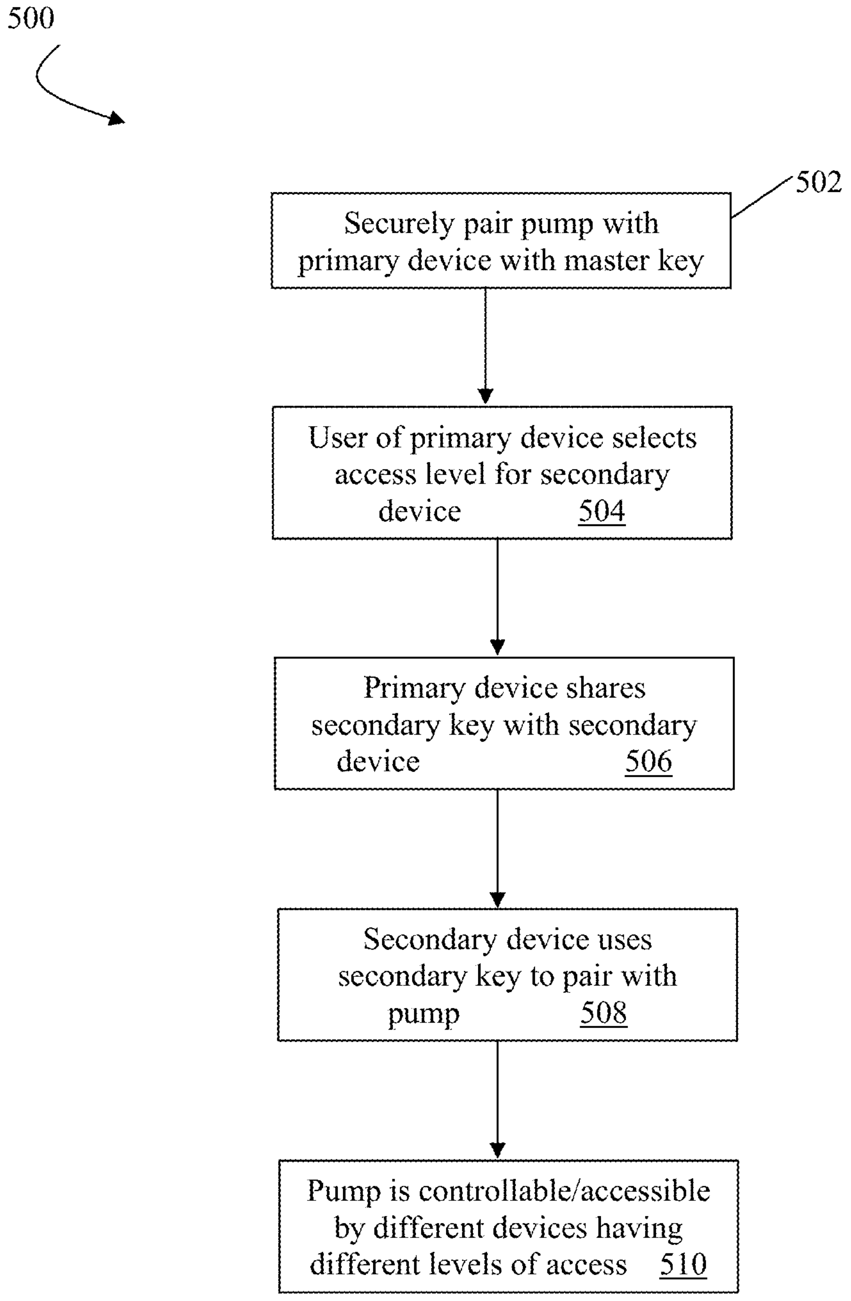
FIG. 9 depicts a flowchart of method steps for providing varying levels of access for wireless control of and/or access to an infusion pump according to the disclosure.

FIG. 9 depicts a flowchart of method steps for providing varying levels of access for wireless control of and/or access to an infusion pump 500 according to an embodiment. At step 502, a primary device is securely paired with an infusion pump. In the described embodiment, this is done via the method of FIG. 7 in which a complex security key is displayed by the pump and entered into the primary device, such as a smartphone. In other embodiments, the primary device can pair with the pump by any other secure means known in the art. In step 502, the pump can also share a master key with the primary device giving full pump access to the primary device. Full pump access can include the ability to provide other devices access including providing varying levels of access. Therefore, at step 504, if a secondary device is to be given a different level of access to the pump, the user of the primary device can select a level of access for the secondary device. The primary device then shares a different, secondary security key with the secondary device rather than the master key at step 506. There can be any number of different secondary keys that provide different levels of access. After the secondary device receives the secondary security key it can initiate a pairing process and pair with the pump at step 508. Steps 504 to 508 can be repeated for any number of secondary devices. Subsequently, at step 510 the pump is capable of being controlled and/or accessed by multiple devices having different levels of access based on the specific security key that was provided by the primary device and used to pair the secondary device with the pump.

The embodiments above disclose various options for enabling easier and more versatile pairing of multiple devices in an infusion pump system by employing a primary device to pair secondary devices with a pump and the ability to provide such secondary devices with varying levels of access to the pump. However, the initial primary device must still be securely paired with the pump. When this pairing is done using the complex security key of FIG. 7, for example, entry of this security key can still be time consuming and is prone to typographical errors. Embodiments herein therefore seek to additionally or alternatively simplify this initial pairing process.

Figure 10:
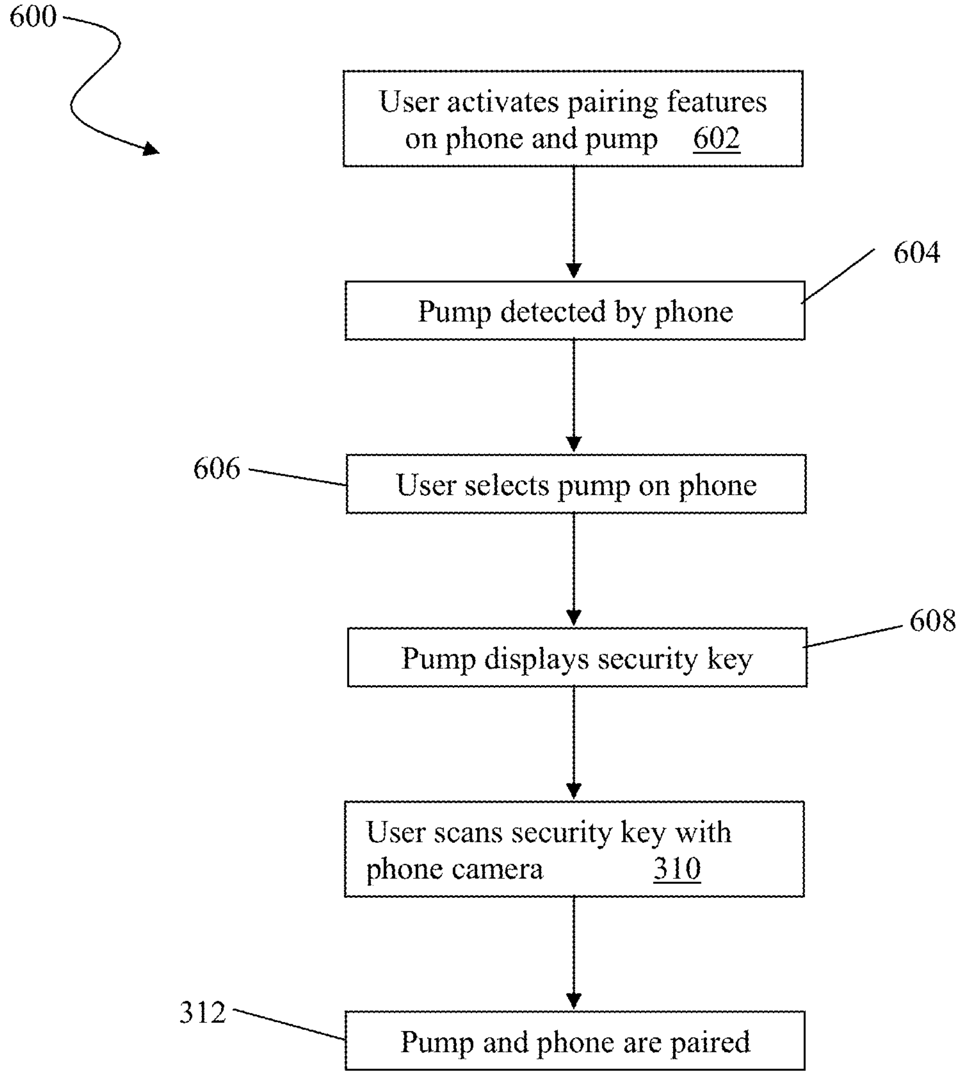
FIG. 10 depicts a flowchart of methods steps for pairing an infusion pump with another device according to the disclosure.

FIG. 10 depict a flowchart of method steps 600 for pairing a device with an infusion pump according to an embodiment. This embodiment is described with respect to pairing a smartphone with an infusion pump, but any other device having a camera capable of taking and processing an image could be employed. Similar to the pairing procedure described above with respect to FIG. 7, a user at step 602 first activates pairing features on the phone and the pump and at step 604 the phone detects the pump. When the user selects the pump on the phone to pair the devices at step 606, the pump displays a security key, such as a complex 16-digit alphanumeric security key at step 608. In this embodiment, rather than the user manually entering the security key into the phone, the user can employ the camera of the phone to scan the security key while it is displayed on the screen of the pump at step 310. This can be done, for example, by using the camera to take a picture of the code and the phone automatically recognizing the characters in the code. In other embodiments, this could be done by scanning a bar code or other indicia displayed on the pump including the security key information. The scanned security data is then used by the phone to complete the pairing process with the pump at step 312. This enables a user to quickly pair the phone with the pump while also eliminating the possibility of typographical errors in transposing the security key into the phone.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106; 10,279,107; 10,357,603; 10,357,606; 10,492,141; 10/541,987; and 10,569,016. commonly owned U.S. Patent Publication Nos. 2009/0287180; 2012/0123230; 2013/0053816; 2014/0276423; 2014/0276569; 2014/0276570; 2018/0021514;

2018/0071454; 2019/0240398; 2019/0307952; 2019/0365997 and 2020/0114076 and commonly owned U.S. patent application Ser. Nos. 16/507,146; 16/725,278; 16/725,337; 16/793,662 and 16/830,415.

Various embodiments of systems, devices, and methods have been described herein.

These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method of pairing devices in an ambulatory infusion pump system, comprising:
- initiating a first pairing procedure to wirelessly pair a user-wearable infusion pump with a primary device;
- receiving secure connection information for wirelessly pairing the user-wearable infusion pump with the primary device at the primary device;
- wirelessly pairing the user-wearable infusion pump with the primary device based on the secure connection information received at the primary device;
- initiating a second pairing procedure to wirelessly pair the user-wearable infusion pump with a secondary device; and
- sharing, from the primary device to the secondary device, a secondary key that is different from the secure connection information used for wirelessly pairing the user-wearable infusion pump with the primary device,
- wherein the secondary security key received from the primary device is used to wirelessly pair the secondary device with the user-wearable infusion pump, and wherein the secondary device is provided with a different level of control of the user-wearable infusion pump than the primary device based on the secondary security key.

2. The method of claim 1, wherein receiving secure connection information at the primary device includes receiving an alphanumeric security key.

3. The method of claim 1, wherein the primary device wirelessly communicates the secondary security key to the secondary device.

4. The method of claim 1, wherein the second pairing procedure is initiated by the primary device.

5. The method of claim 1, wherein the second pairing procedure is initiated by the secondary device.

6. The method of claim 1, wherein the second pairing procedure is initiated by the user-wearable infusion pump.

7. The method of claim 1, wherein the different level of control of the user-wearable infusion pump for the secondary device includes one of read-only access to data or bolus-only capability for pump programing.

8. The method of claim 1, wherein receiving the secure connection information for wirelessly pairing the user-wearable infusion pump with the primary device at the primary device includes the secure connection information being manually entered into the primary device, and wherein sharing the secondary security key with the secondary device includes the secondary device being wirelessly paired with the user-wearable infusion pump without the secondary security key being manually entered into the secondary device.

9. The method of claim 1, wherein:
the primary device is a smartphone; and
the secondary device is an electronic watch.

10. The method of claim 1, further comprising:
displaying the secure connection information at the user-wearable infusion pump (i) responsive to initiating the first pairing procedure and (ii) prior to receiving the secure connection information.

11. A method of pairing devices in an ambulatory infusion pump system, comprising:
initiating a first pairing procedure to wirelessly pair a user-wearable infusion pump with a primary device;
executing the first pairing procedure to wirelessly pair the user-wearable infusion pump with the primary device based on secure connection information, the first pairing procedure requiring a security protocol be executed on the primary device;
initiating a second pairing procedure to wirelessly pair the user-wearable infusion pump with a secondary device; and
sharing, from the primary device to the secondary device, a secondary security key that is different from the secure connection information used for wirelessly pairing the user-wearable infusion pump with the primary device,
wherein the secondary security key received from the primary device is used to wirelessly pair the secondary device with the user-wearable infusion pump without executing the security protocol on the secondary device, and wherein the secondary device is provided with a different level of control of the user-wearable infusion pump than the primary device based on the secondary security key.

12. The method of claim 11, wherein the secure connection information is an alphanumeric security key.

13. The method of claim 11, wherein the primary device wirelessly communicates the secondary security key to the secondary device.

14. The method of claim 11, wherein the second pairing procedure is initiated by the primary device.

15. The method of claim 11, wherein the second pairing procedure is initiated by the secondary device.

16. The method of claim 11, wherein the second pairing procedure is initiated by the user-wearable infusion pump.

17. The method of claim 11, wherein the different level of control of the user-wearable infusion pump for the secondary device includes one of read-only access to data or bolus-only capability for pump programing.

18. The method of claim 11, further comprising:
receiving the secure connection information for wirelessly pairing the user-wearable infusion pump with the primary device at the primary device, wherein the receiving includes the secure connection information being manually entered into the primary device, and wherein sharing the secondary security key with the secondary device includes the secondary device being wirelessly paired with the user-wearable infusion pump without the secondary security key being manually entered into the secondary device.

19. The method of claim 18, further comprising:
displaying the secure connection information at the user-wearable infusion pump (i) responsive to initiating the first pairing procedure and (ii) prior to receiving the secure connection information.

20. The method of claim 11, wherein:
the primary device is a smartphone; and
the secondary device is an electronic watch.

21. A control device configured to control an ambulatory infusion pump system, the control device comprising:
a processor configured to execute a plurality of operations associated with connecting with a user-wearable infusion pump such that the processor is configured to:
initiate a first pairing procedure to wirelessly pair the user-wearable infusion pump with the control device;
receive, at the control device, secure connection information for wirelessly pairing the user-wearable infusion pump with the control device;
wirelessly pair the user-wearable infusion pump with the control device based on the secure connection information;
initiate a second pairing procedure to wirelessly pair the user-wearable infusion pump with a secondary device; and
share, from the control device to the secondary device, a secondary key that is different from the secure connection information used for wirelessly pairing the user-wearable infusion pump with the control device,
wherein the secondary security key shared by the control device to the secondary device is used to wirelessly pair the secondary device with the user-wearable infusion pump, and wherein the secondary device is provided with a different level of control of the user-wearable infusion pump than the control device based on the secondary security key.

* * * * *